United States Patent
Takagaki et al.

(10) Patent No.: US 10,329,224 B2
(45) Date of Patent: Jun. 25, 2019

(54) METHOD FOR PRODUCTION OF CONJUGATED DIOLEFIN

(75) Inventors: Kazuhiro Takagaki, Tokyo (JP); Hiroyuki Yano, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/383,479

(22) PCT Filed: Mar. 13, 2012

(86) PCT No.: PCT/JP2012/056388
§ 371 (c)(1),
(2), (4) Date: Dec. 10, 2014

(87) PCT Pub. No.: WO2013/136434
PCT Pub. Date: Sep. 19, 2013

(65) Prior Publication Data
US 2015/0126788 A1  May 7, 2015

(51) Int. Cl.
| | | |
|---|---|---|
| C07C 7/11 | (2006.01) |
| C07C 5/48 | (2006.01) |
| C07C 7/00 | (2006.01) |
| C07C 7/10 | (2006.01) |
| B01J 23/887 | (2006.01) |

(52) U.S. Cl.
CPC ............. C07C 7/11 (2013.01); B01J 23/8872 (2013.01); C07C 5/48 (2013.01); C07C 7/10 (2013.01); B01J 2523/00 (2013.01); C07C 2521/08 (2013.01); C07C 2523/02 (2013.01); C07C 2523/04 (2013.01); C07C 2523/10 (2013.01); C07C 2523/18 (2013.01); C07C 2523/28 (2013.01); C07C 2523/745 (2013.01); C07C 2523/755 (2013.01); C07C 2523/887 (2013.01)

(58) Field of Classification Search
None
See application file for complete search history.

(56) References Cited

U.S. PATENT DOCUMENTS

| | | | | |
|---|---|---|---|---|
| 2,385,705 A | * | 9/1945 | Huffman | C07C 7/10 585/856 |
| 2,409,250 A | * | 10/1946 | Cannon | C07C 7/11 585/838 |
| 3,423,385 A | * | 1/1969 | Bebb | C07C 7/005 526/173 |
| 3,474,155 A | * | 10/1969 | Woerner | C07C 7/11 585/380 |
| 3,663,641 A | | 5/1972 | Hanson | |
| 3,943,185 A | * | 3/1976 | Tschopp | C07C 5/48 585/380 |
| 4,049,742 A | | 9/1977 | Weitz et al. | |
| 4,595,788 A | | 6/1986 | Yamamoto et al. | |
| 6,175,049 B1 | | 1/2001 | Stuwe et al. | |
| 2007/0244349 A1 | | 10/2007 | Crone et al. | |
| 2007/0256920 A1 | * | 11/2007 | Kanauchi | B01D 3/40 203/2 |
| 2011/0034330 A1 | * | 2/2011 | Czaja | B01J 23/002 502/243 |
| 2012/0130137 A1 | * | 5/2012 | Orita | B01J 23/002 585/621 |

FOREIGN PATENT DOCUMENTS

| | | |
|---|---|---|
| JP | 47-34207 A | 11/1972 |
| JP | 60-115532 A | 6/1985 |
| JP | 60-126235 A | 7/1985 |
| JP | 61-18733 A | 1/1986 |
| JP | 2000-72694 A | 3/2000 |
| JP | 2003-138276 A | 5/2003 |
| JP | 2010-90082 A | 4/2010 |
| JP | 2010-90083 A | 4/2010 |
| JP | 2010-120933 A | 6/2010 |

OTHER PUBLICATIONS

The European Search Report, dated Feb. 19, 2015, for European Application No. 12871461.5.
International Search Report for PCT/JP2012/056388 dated Jun. 5, 2012.
Written Opinion of the International Searching Authority for PCT/JP2012/056388 dated Jun. 5, 2012.

* cited by examiner

*Primary Examiner* — Philip Y Louie
(74) *Attorney, Agent, or Firm* — Birch, Stewart, Kolasch & Birch, LLP

(57) ABSTRACT

An object of the present invention is to provide a method for production of a high purity conjugated diolefin. The method for production of a conjugated diolefin of the present invention comprises steps of supplying a source gas containing a C4 or higher monoolefin and an oxygen-containing gas into a reactor, bringing a catalyst into contact with the gas mixture, compressing a gas containing a conjugated diolefin produced by an oxidative dehydrogenation reaction to obtain a liquefied gas and rinsing the liquefied gas with water.

20 Claims, No Drawings

METHOD FOR PRODUCTION OF CONJUGATED DIOLEFIN

TECHNICAL FIELD

The present invention relates to a method for production of a conjugation diolefin.

BACKGROUND ART

A method employed for industrially producing a conjugated diolefin, for example, 1,3-butadiene (hereinafter also referred to as "butadiene") is to extract BBP (mainly a hydrocarbon mixture having 3 to 5 carbon atoms) obtained from naphtha cracking into a solvent and selectively remove butane, butene, acetylenes, high boiling components, low boiling components, etc.

In contrast, Patent Documents 1 and 2 disclose methods for producing butadiene from butene. In these methods, butene is subjected to oxidative dehydrogenation and quenched and the moisture is removed therefrom, followed by absorbing butadiene using a solvent for collection. Examples of easy methods for removing moisture which are commonly used include distillation and adsorption. Patent Documents 3 and 4 describe a method in which right butene is subjected to gas phase catalytic oxidative dehydrogenation in a fixed bed, the produced gas is cooled, high boiling by-products are removed and the aldehyde contained in the cooled gas is removed.

LIST OF PRIOR ART DOCUMENTS

Patent Document

Patent Document 1
Japanese Patent laid-Open No. 2010-90082 Patent Document 2
Japanese Patent laid-Open No. 2010-90083 Patent Document 3
Japanese Patent laid-Open No. 60-115532 Patent Document 4
Japanese Patent laid-Open No. 60-126235

SUMMARY OF INVENTION

Problems to be Solved by the Invention

In the conventional method of producing butadiene from butene by an oxidative dehydrogenation reaction, the moisture is supposedly separated by distillation from the gas produced by the oxidative dehydrogenation reaction. A problem thereof is that large amounts of inert gases such as nitrogen, oxygen, carbon dioxide are present in the gas produced in the reaction in addition to the butadiene to be distilled. Also, when the gas produced in the reaction is distilled, the liquefaction of the produced gas by compression requires also liquefying components to be removed such as moisture, demanding an extremely high compressibility, which thus is inefficient considering the energy efficiency required for the compression. Meanwhile, an adsorbent suitable for capturing moisture is used for adsorption dehydration, but at the time of adsorption operation, the adsorbent adsorbs the components produced in the reaction, in particular high boiling components, in addition to water. For this reason, there are problems such as significantly reduced dehydration capability of an adsorbent or a broken through adsorbent in a short period of time because of the adsorption of high boiling components. To obviate these problems, the switchover operation of dehydrators can be performed by providing a plurality of dehydrators containing an adsorbent to periodically regenerate dehydrators with a reduced dehydration capability or blocked dehydrators. However, this instance complicates the process and is inevitably inefficient when operated for a long time.

In the oxidative dehydrogenation reaction of butene, a variety of by-products are produced other than the intended butadiene to be produced. Examples of the by products include oxides and high boiling components such as furan, acrolein, acrylic acid, acetaldehyde, acetic acid, phenol, benzaldehyde and benzoic acid. Examples of a method for removing, among these, acidic components such as acrylic acid and acetic acid include extraction. The aldehyde removal steps described in Patent Documents 3 and 4 are each a method which uses an organic acid aqueous solution as an extraction solvent. However, since the extraction method which uses water is a removal method by a physical interaction, which is the property of dissolution of an acidic component in water, the method has the following drawbacks: the components to be removed cannot be removed more than the partition equilibrium concentration in water and the concentration of the component to be removed cannot be made lower than the vapor pressure thereof. Further, since the gas-liquid extraction method in which impurities in a cooled produced gas are extracted into water is essentially inefficient, the column diameter of a water extraction column must be made large in order to assure an extraction amount per unit time equivalent to that of the liquid-liquid extraction method, expanding the construction costs, and thus the method is also economically disadvantageous.

Thus, no method described in the above patent Documents is capable of efficiently producing a high purity conjugated diolefin.

Consequently, an object of the present invention is to provide a method for producing a high purity conjugated diolefin, for example, butadiene, by efficiently removing acetaldehyde in the step of purifying a gas containing a conjugated diolefin, for example, butadiene, produced by an oxidative dehydrogenation reaction of a raw material containing a monoolefin having four or more carbon atoms (hereinafter also referred to as "C4" or higher monoolefin).

Means for Solving the Problems

The present inventors have conducted extensive studies to achieve the above object and have found that a high purity conjugated diolefin, for example, butadiene, can be produced by liquefying a reaction produced gas containing a conjugated diolefin, for example, butadiene, produced by an oxidative dehydrogenation reaction, and efficiently removing acetaldehyde by rinsing the liquefied gas with water.

More specifically, the present invention is as follows.

[1]

A method for production of a conjugated diolefin comprising steps of supplying a source gas containing a C4 or higher monoolefin and an oxygen-containing gas into a reactor, bringing a catalyst into contact with the gas mixture, compressing a gas containing a conjugated diolefin produced by an oxidative dehydrogenation reaction to obtain a liquefied gas and rinsing the liquefied gas with water.

[2]

The method for production of the conjugated diolefin according to [1], further comprising steps of:
cooling the gas containing the conjugated diolefin, and
allowing the gas containing the conjugated diolefin to be absorbed in a solvent, followed by stripping the gas containing the conjugated diolefin from the solvent.

[3]

The method for production of the conjugated diolefin according to [1] or [2] comprising the following steps of (1) to (6) in this order:
step (1): a step of supplying a source gas containing a C4 or higher monoolefin and an oxygen-containing gas into a reactor and bringing a catalyst into contact with the gas mixture to obtain a gas containing a conjugated diolefin by an oxidative dehydrogenation reaction,
step (2): a step of cooling the gas containing the conjugated diolefin in a quench column,
step (3): a step of allowing the gas containing the conjugated diolefin to be absorbed in a solvent, subsequently stripping the gas containing the conjugated diolefin from the solvent, followed by compressing the gas to obtain a liquefied gas,
step (4): a step of rinsing the liquefied gas with water, step (5): a step of removing the water from the liquefied gas, and
step (6): a step of removing a high boiling component from the liquefied gas.

[4]

The method for production of the conjugated diolefin according to [3],
wherein the liquefied gas obtained in the step (3) contains acetaldehyde, and
the acetaldehyde is dissolved in the water in the step (4).

[5]

The method for production of the conjugated diolefin according to [3] or [4], further comprising, before the step (4) and/or after the step (6), a step of:
allowing the liquefied gas to be absorbed in a higher polar solvent than the solvent of the step (3), followed by stripping the gas containing the conjugated diolefin from the higher polar solvent.

[6]

The method for production of the conjugated diolefin according to [5], wherein the high polar solvent contains at least one selected from the group consisting of N-alkyl-substituted lower fatty acid amide, a nitrile compound and a heterocyclic compound.

[7]

The method for production of the conjugated diolefin according to any one of [1] to [6], wherein the source gas contains n-butene.

Advantages of the Invention

According to the production method of the present invention, a high purity conjugated diolefin, for example, butadiene, can be produced by efficiently removing acetaldehyde from a gas containing a conjugated diolefin produced by an oxidative dehydrogenation reaction of a raw material containing a C4 or higher monoolefin.

MODE FOR CARRYING OUT THE INVENTION

Hereinafter, the embodiments for implementing the present invention (hereinafter referred to as the present embodiments) will be described in detail. Note that the present invention is not limited to the following embodiments but can be implemented by various modifying them within the scope of the gist thereof. A method required to produce purified butadiene is described below.

Method for Producing Conjugated Diolefin

The method for production of the conjugated diolefin of the present embodiment comprises steps of supplying a source gas containing a C4 or higher monoolefin and an oxygen-containing gas into a reactor, bringing a catalyst into contact with the gas mixture, compressing a gas containing a conjugated diolefin produced by an oxidative dehydrogenation reaction to obtain a liquefied gas and rinsing the liquefied gas with water.

Further, the method for production of the conjugated diolefin of the present embodiment preferably further comprises the steps of cooling the gas containing the conjugated diolefin, and allowing the gas containing the conjugated diolefin to be absorbed in a solvent, followed by stripping the gas containing the conjugated diolefin from the solvent.

Furthermore, the method for production of the conjugated diolefin of the present embodiment more preferably comprises the following steps of (1) to (6) in this order.

Step (1): a step of supplying a source gas containing a C4 or higher monoolefin and an oxygen-containing gas into a reactor and bringing a catalyst into contact with the gas mixture to obtain a gas containing a conjugated diolefin by an oxidative dehydrogenation reaction.

Step (2): a step of cooling the gas containing the conjugated diolefin in a quench column.

Step (3): a step of allowing the gas containing the conjugated diolefin to be absorbed in a solvent, subsequently emitting the gas containing the conjugated diolefin from the solvent, followed by compressing the gas to obtain a liquefied gas.

Step (4): a step of rinsing the liquefied gas with water.

Step (5): a step of removing the water from the liquefied gas.

Step (6): a step of removing a high boiling component from the liquefied gas.

Still furthermore, in the method for production of the conjugated diolefin of the present embodiment, it is preferred that the liquefied gas obtained in the step (3) contains acetaldehyde, and the acetaldehyde is dissolved in the water in the step (4).

Still furthermore, the method for production of the conjugated diolefin of the present embodiment preferably further comprises a step, before step (4) and/or after step (6), of allowing the liquefied gas to be absorbed in a higher polar solvent than the solvent of the step (3), followed by stripping the gas containing the conjugated diolefin from the high polar solvent.

The above-mentioned comprised steps enable a production of a high purity conjugated diolefin by even more efficiently removing acetaldehyde.

Hereinbelow, the method for production of the conjugated diolefin of the present embodiment is described in detail with reference to an example of the butadiene production method.

[a] Step of Obtaining a Butadiene-Containing Gas

The production method of the present embodiment comprises steps of supplying a source gas containing a C4 or higher monoolefin and an oxygen-containing gas into a reactor and bringing a catalyst into contact with the gas mixture to obtain a gas containing a conjugated diolefin by an oxidative dehydrogenation reaction.

(1) Source Gas

The source gas contains a C4 or higher monoolefin. Examples of the C4 or higher monoolefin include n-butene, isobutene, n-pentene, methylbutene, n-hexene, methylhexene, dimethylbutene and mixtures thereof. In the light of production efficiency of butadiene, the source gas preferably contains n-butene (specifically, 1-butene and/or 2-butene). A preferably used as an industrial n-butene source is BBSS obtained after separating butadiene and isobutene from BBP. The ratio of 1-butene and 2-butene is not limited and 1-butene can be used within the range of 0 to 100% by weight and 2-butene can be used within the range of 100 to 0% by weight. 2-Butene is present in the trans form and the cis form. The ratio of the trans form and the cis form can be any within the range of 100 to 0% by weight, 0 to 100% by weight, respectively. The source gas can contain a small amount of butadiene and isobutene. Butadiene, based on n-butene, can be contained in preferably 5% by weight or less, more preferably 3% by weight or less, further preferably 1% by weight or less. Isobutene, based on n-butene, can be contained in preferably 10% by weight or less, more preferably 0.1 to 6% by weight, further preferably 0.5 to 3% by weight. The source gas may contain n-butane, isobutane, hydrocarbons having three or less carbon atoms or hydrocarbons having five or more carbon atoms. In the source gas, the concentration of n-butene is preferably 40% by weight or more, more preferably 50% by weight or more, further preferably 60% by weight or more.

The separation of butane from a C4 fraction by extractive distillation using a solvent before supplying a source gas into a reactor is another preferred method. Usable solvents for the extractive distillation to separate butane are those having a boiling point of 100 to 210° C. Specific examples of such a solvent include octane, nonane, decane, ethylcyclohexane, octene, nonene, toluene, ethylbenzene, o-xylene, m-xylene, p-xylene, mixed xylene, cumene and vinylcyclohexene. Among these, octane, nonane, decane, ethylcyclohexane, toluene, ethylbenzene, xylene, cumene and pseudocumene are preferably used.

The source gas is not necessarily highly purified, and any mixture or an industrial grade can be used as the source gas. For example, the following source gases can be used: a residual component (BBS) obtained by extracting butadiene from BBP byproduced in naphtha thermal cracking; a residual component, BBSS, obtained by further separating isobutylene from the residual component; a C4 fraction byproduced in fluidized catalytic cracking (FCC) of a heavy oil fraction; a residual component obtained by further separating isobutene from the C4 fraction; a C4 component obtained by dehydrogenation or oxidative dehydrogenation of n-butane; 1-butene obtained by dimerizing ethylene; or a C4 fraction byproduced in the catalytic conversion of ethylene or ethanol; or a residual component obtained by further separating isobutene from the C4 fraction. Isobutene can be separated by a method in which it is converted to a compound having eight carbon atoms by the skeletal isomerization, selective adsorption or dimerization reaction to tert-butyl alcohol, methyl-tert-butyl ether, ethyl-tert-butyl ether or n-butene. Usable ethylene are those obtained by naphtha thermal cracking, ethane thermal cracking or dehydration of ethanol, and usable ethanol are industrial ethanol and biomass ethanol. Biomass ethanol is ethanol obtained from biomass, and specific examples include ethanol obtained by fermentation of sugarcane, corn, and the like and ethanol obtained from woody resources such as scrap wood, thinner timber, rice straw, and agricultural products.

The above-mentioned source gas containing a C4 or higher monoolefin and an oxygen-containing gas are supplied into a reactor. The source gas and the oxygen-containing gas are also collectively referred to as "raw material mixed gas."

The oxygen-containing gas is described in detail in the (3) Reaction conditions paragraph to be described later.

The n-butene concentration in the raw material mixed gas supplied to a reactor is preferably 2% by volume or more based on 100% by volume of the raw material mixed gas containing at least n-butene and oxygen from the viewpoint of the productivity of butadiene, and preferably 30% by volume or less from the viewpoint of suppressing the load to a catalyst. The n-butene concentration is more preferably in the range of 3 to 25% by volume, and further preferably 5 to 20% by volume. When the n-butene concentration is in the above range, there is a tendency that the accumulation of a reaction product and the precipitation of a coke on the catalyst can be suppressed and the catalyst life becomes longer, and also the production volume of butadiene will be satisfactory.

The raw material mixed gas may contain paraffins, water, steam, hydrogen, nitrogen, carbon dioxide, carbon monoxide, and the like. Examples of paraffins can include methane, ethane, propane, butane, pentane, hexane, heptane, octane, and nonane. After butadiene which is an objective product is separated from a reaction product, it is also possible to recycle at least part of recovered unreacted butene to a reactor.

Another preferred embodiment is that the raw material mixed gas contains preferably 30% by volume or less, more preferably 20% by volume, further preferably 10% by volume of water.

(2) Reactor

The production of butadiene by the oxidative dehydrogenation of a C4 or higher monoolefin can be performed by any of the fluidized bed reaction system, the fixed bed reaction system, and the moving bed reaction system. In the lights of removing the generated reaction heat and extracting and adding a catalyst, the production of butadiene can be preferably performed by the fluidized bed reaction system. The fluidized bed reactor has a structure having a gas distributor, an inserted object, and a cyclone as the main components in the reactor, wherein the catalyst is fluidized to bring it into contact with a gas which is a raw material. If it is a fluidized-bed reactor described in the Fluidized Bed Handbook (published by Baifukan, 1999) or the like, it can be used. A reactor of the cellular fluidized bed system is particularly suitable. The heat of reaction generated can be removed using a cooling pipe placed in the reactor.

The cooling pipe is disposed in the thick layer and the thin layer in the reactor and operated to achieve the intended temperatures.

(3) Reaction Conditions

A source gas containing a C4 or higher monoolefin and an oxygen-containing gas are supplied into a reactor and a catalyst is brought into contact with the gas mixture to produce a gas containing butadiene by an oxidative dehydrogenation reaction. The conditions for the oxidative dehydrogenation reaction are described below.

In the oxidative dehydrogenation reaction, a C4 or higher monoolefin and oxygen are subjected to the reaction. Air is generally used as the oxygen-containing gas, i.e., the oxygen source, but it is also possible to use a gas having an increased oxygen concentration prepared, for example, by mixing oxygen with air or a gas having a decreased oxygen concentration prepared, for example, by mixing air with nitrogen, helium or a gas after separating hydrocarbon compounds such as butadiene, n-butene, n-butane, isobutane from the reaction produced gas. Further, a gas having an increased oxygen concentration prepared, for example, by a separation method using an oxygen separation membrane, and still furthermore, a gas having a decreased oxygen concentration prepared by the separation method can be used.

In the raw material mixed gas, a molar ratio of oxygen to n-butene is preferably in the range of 0.5 to 1.5 (in terms of air/n-butene ratio of 2.5 to 7.5), more preferably 0.6 to 1.3 (in terms of air/n-butene ratio of 3.0 to 6.5).

A method for introducing a C4 or higher monoolefin and oxygen is not limited, and an introduction method in which the gases subjected to reaction are within the ratio as described above is preferable. A source gas containing a C4 or higher monoolefin may be previously mixed with an oxygen-containing gas (for example, air, a gas having an increased oxygen concentration, or a gas having an decreased oxygen concentration), before these gases are introduced into a reactor filled with a catalyst, or each of these gases may be independently introduced into the reactor. Although the gases subjected to reaction can be increased to a predetermined reaction temperature after they are introduced into the reactor, the gases are usually preheated before being introduced into the reactor in order to allow them to continuously and efficiently react with each other. For example, n-butene which is liquid at ordinary temperature (5 to 35° C.) is preferably subjected to reaction after it is gasified with a gasifier having a heating unit using steam, a heat transfer coil, or the like.

When a fluidized bed reactor is used for the reaction, the temperature of the thick layer in the fluidized bed reactor is preferably 320 to 400° C., and the temperature of the thin layer is preferably controlled at −50 to +20° C. with respect to the temperature of the thick layer. When the temperature of the thick layer is controlled at 320° C. or higher, the thick layer temperature is easily maintained and the reactor can be stably operated in continuation while maintaining the conversion of the monoolefin. When the thick layer temperature is controlled at 400° C. or lower, the combustion decomposition of the produced conjugated diolefin can be controlled. The temperature of the thick layer in the fluidized bed reactor is preferably in the range of 330 to 390° C., more preferably 340 to 380° C. Since the reaction for producing butadiene is an exothermic reaction, the temperatures of the thick layer and the thin layer in a fluidized bed reactor are controlled so that the above temperature ranges are achieved by removing the reaction heat with a cooling pipe, supplying heat with a heating device or using the residual heat of the supplied source gas.

The reaction pressure is preferably 0.01 to 0.4 MPaG, more preferably 0.02 to 0.3 MPaG, and further preferably 0.03 to 0.2 MPag. The contact time between a raw material mixed gas and a catalyst is in the range of 0.5 to 20 g·sec/cc, preferably in the range of 1 to 10 g·sec/cc. The contact time herein is defined by the following formula.

$$\text{Contact time (g·sec/cc)} = \frac{W \times 60 \times 273.15 \times (P \times 1000 + 101.325)}{F \times (273.15 + T) \times 101.325}$$ [Expression 1]

W: the filling amount of a catalyst (g); F: the flow rate of a raw material mixed gas (cc/min, in terms of NTP); T: the reaction temperature (° C.); and P: the reaction pressure (MPaG).

Contact of the catalyst with the raw material mixed gas in the reactor produces butadiene from n-butene, and the gas containing the produced butadiene flows out of a reactor exit. The oxygen concentration in the reactor outlet gas is preferably maintained in the range of 0.01 to 3.0% by volume, more preferably maintained in the range of 0.05 to 2.0% by volume. Reduction of the catalyst in the reactor and decomposition of the objective product can be effectively prevented by maintaining the oxygen concentration in the reactor outlet gas within the above ranges, whereby butadiene can be produced stably. Since the oxygen concentration in the reactor outlet gas affects the decomposition and the second order reaction of the butadiene in the reactor, maintaining the concentration at 2.0% by volume or less is a preferred embodiment. The oxygen concentration in the reactor outlet gas can be adjusted by changing the amount of n-butene contained in the source gas to be supplied to the reactor, the amount of an oxygen-containing gas used as the oxygen source, reaction temperature, pressure in the reactor, the amount of a catalyst, and the total gas volume to be supplied to the reactor. The oxygen concentration in the reactor outlet gas is preferably controlled by changing the amount of an oxygen-containing gas used as the oxygen source to be supplied to the reactor, for example, the amount of air.

The oxygen concentration in the reactor outlet gas can be measured by gas chromatography provided with a heat conduction type detector (TCD), or a galvanic cell type oxygen concentration analyzer.

(4) Catalyst

The catalyst used in the present embodiment is described in detail below.

(4-1) Structure

The catalyst used in the present embodiment is, in the light of obtaining butadiene by a fluidized bed reaction in a comparatively high yield, a catalyst in which an oxide is supported on a carrier, and preferably contains Mo, Bi, and Fe. The composition of Mo, Bi, and Fe is adjusted so as to form an appropriate oxide, and the oxidative dehydrogenation from n-butene to butadiene is probably performed by the lattice oxygen in this oxide. Generally, when the lattice oxygen in the catalyst is consumed in the oxidative dehydrogenation, oxygen holes will be produced in the oxide. As a result, the reduction of the oxide also advances with the progress of the reaction to deactivate the catalytic activity. Therefore, it is necessary to quickly reoxidize the oxide which has undergone reduction in order to maintain the catalytic activity. The oxide containing Mo, Bi, and Fe is probably excellent not only in the reactivity in the oxidative dehydrogenation from n-butene to butadiene but also in the reoxidation function of dissociatively adsorbing oxygen in the gaseous phase to take it into the oxide to regenerate the consumed lattice oxygen. Therefore, the reoxidation function of lattice oxygen is probably maintained even when the reaction is carried out over a long period of time, and the catalyst can stably produce butadiene from n-butene without being deactivated.

The use of a catalyst in which an oxide containing Mo, Bi, and Fe is supported on a carrier for production of butadiene by a fluidized bed system is advantageous to suppress the formation of an oxygen-containing compound by the combustion decomposition and the second order reaction of butadiene which is a product, and butadiene can be obtained in high yield. Details are not known, but the following reasons are considered: (1) since the acidity of the catalyst is suitable, the combustion decomposition and the second order reaction of butadiene on the catalyst are low; and (2) since the adsorption ability of a reaction active point to the produced butadiene is small, butadiene is probably eliminated quickly after it is produced and before it undergoes decomposition and reaction at the reaction active point.

Since Mo, Bi, and Fe are easily form an appropriate oxide, the composition ratio of these atoms is probably as follows: an atomic ratio of Bi of p and an atomic ratio of Fe of q to an atomic ratio of Mo of 12 in the oxide satisfy $0.1 \leq p \leq 5$ and $0.5 \leq q \leq 8$.

When the oxide contains metals other than Mo, Bi, and Fe, it is preferably represented by the empirical formula: $Mo_{12}Bi_pFe_qA_aB_bC_cD_dE_eO_x$
wherein A is at least one element selected from the group consisting of nickel and cobalt; B is at least one element selected from the group consisting of alkali metal elements; C is at least one element selected from the group consisting of magnesium, calcium, strontium, barium, zinc, and manganese; D is at least one rare earth element; E is at least one element selected from the group consisting of chromium, indium, and gallium; 0 is oxygen; p, q, a, b, c, d, e, and x represent an atomic ratio of bismuth, iron, A, B, C, D, E, and oxygen, respectively, to 12 molybdenum atoms; $0.1 \leq p \leq 5$, $0.5 \leq q \leq 8$, $0 \leq a \leq 10$, $0.02 \leq b \leq 2$, $0 \leq v \leq 5$, $0 \leq d \leq 5$, and $0 \leq e \leq 5$ are satisfied; and x is an atomic number of oxygen required for satisfying a valence requirement of other elements present. As used herein the "empirical formula" is a formula which represents the composition consisting of the atomic ratios of metals included in the formula and oxygen required depending on the total of the atomic ratios and the oxidation numbers. Since it is substantially impossible to specify the atomic number of oxygen in the oxide containing metals which can take various oxidation numbers, the number of oxygen is formally represented by "x". For example, when the oxide is obtained by preparing a slurry containing a Mo compound, a Bi compound, and a Fe compound and drying and/or firing the slurry, the atomic ratio of the metals contained in the slurry can be regarded as substantially equal to the atomic ratio of the metals in the resulting oxide. Therefore, the empirical formula of the resulting oxide is obtained by adding $O_x$ to the compositional formula of the prepared slurry. Note that, in the present specification, the formula representing the components controlled intentionally and the ratio thereof like the prepared composition of the slurry as described above is referred to as a "compositional formula". Therefore, in the case of the above-described example, the "compositional formula" is obtained by excluding $O_x$ from the empirical formula.

Although the role of the components represented by A, B, C, D, and E is not limited but in the field of the oxide catalyst using Mo, Bi, and Fe as essential components, the role is generally presumed as follows. Probably, A and E improve the activity of the catalyst; B and C stabilize the structure of the appropriate oxide containing Mo, Bi, and Fe; and D influences the reoxidation of the oxide. When p, q, a, b, c, d, and e are in preferred ranges, these effects can be expected to be much higher. In the above composition formula, as a more preferred composition, $0.1 \leq p \leq 0.5$, $1.5 \leq q \leq 3.5$, $1.7 \leq a \leq 9$, $0.02 \leq b \leq 1$, $0.5 \leq c \leq 4.5$, $0.02 \leq d \leq 0.5$, and $0 \leq e \leq 4.5$ are satisfied. As a still more preferred composition, B is rubidium, potassium or cesium; C is magnesium; and D is cerium; and $0.15 \leq p \leq 0.4$, $1.7 \leq q \leq 3$, $2 \leq a \leq 8$, $0.03 \leq b \leq 0.5$, $1 \leq c \leq 3.5$, $0.05 \leq d \leq 0.3$, and $0 \leq e \leq 3.5$ are satisfied. When A is nickel; B is rubidium, potassium or cesium; C is magnesium; and D is cerium, there is a tendency that the yield of a conjugated diolefin, e.g., butadiene, is higher; its combustion decomposition is well suppressed; and the resistance to reduction degradation can be imparted to the catalyst.

The carrier can be effectively used in an amount in the range of 30 to 70% by weight, preferably in the range of 40 to 60% by weight based on the sum total of the carrier and the oxide. The supported catalyst containing the oxide containing Mo, Bi, and Fe can be obtained by a known method, for example a method comprising a first step of preparing a raw material slurry, a second step of spray drying the raw material slurry, and a third step of firing the dried product obtained in the second step. The carrier is preferably silica, alumina, titania, or zirconia, and a more suitable carrier is silica. Silica is an inert carrier compared with other carriers, and it has a good binding action with the catalyst without reducing the activity and selectivity of the catalyst to an objective product. In addition, physical properties suitable to fluidized bed reaction such as particle shape, size, distribution, fluidity, and mechanical strength can be imparted to the oxide by supporting the oxide on the carrier.

(4-2) Method for Preparing the Catalyst

A Method for Preparing the Catalyst Used in the present embodiments preferably comprises a first step of preparing a raw material slurry, a second step of spray drying the raw material slurry, and a third step of firing the dried product obtained in the second step. The preferred embodiments of the method for preparing the catalyst is described below with reference to a catalyst containing Mo, Bi and Fe.

The raw material slurry is obtained by preparing a catalyst raw material in the first step. Element sources for each element constituting the catalyst, for example, molybdenum, bismuth, iron, nickel, cobalt, an alkali metal element, magnesium, calcium, strontium, barium, zinc, manganese, a rare earth element, chromium, indium, and gallium include an ammonium salt, a nitrate, a hydrochloride, a sulfate, an organic acid salt, and the like, which are soluble in water or nitric acid. Particularly, an ammonium salt is preferred as a molybdenum source, and nitrate is preferred as an element source for each element of bismuth, iron, nickel, an alkaline earth, magnesium, zinc, manganese, and a rare earth element. As described above, oxides such as silica, alumina, titania, and zirconia can be used. Silica is used as a suitable carrier, and silica sol is preferred as a silica source. With respect to an impurity in silica sol, there is preferably used a silica sol containing 0.04 atoms or less of aluminum per 100 atoms of silicon, more preferably a silica sol containing 0.02 atoms or less of aluminum per 100 atoms of silicon. The raw material slurry can be prepared, for example, by adding an ammonium salt of molybdenum dissolved in water to silica sol and then adding thereto a solution of a nitrate of each element of bismuth, a rare earth element, iron, nickel, magnesium, zinc, manganese, and an alkaline earth element in water or a nitric acid solution. Thus, the raw material slurry can be prepared. In that case, the order of the addition as described above can also be changed.

In the second step, the raw material slurry obtained in the first step is spray dried to obtain spherical particles. The atomization of the raw material slurry can be performed by a method generally performed industrially such as a centrifugal system, a two fluid nozzle system, and a high pressure nozzle system. Particularly, it is preferable to perform the atomization by a centrifugal system. Next, the obtained particles are dried. Air that is heated with steam, electric heater, or the like is preferably used as the drying heat source. The temperature of a drier entrance is preferably in the range of 100 to 400° C., and more preferably in the range of 150 to 300° C.

In the third step, a desired catalyst is obtained by firing the dried particles obtained in the second step. Preferably, the dried particles are optionally pre-fired in the temperature range of 150 to 500° C., and then fired in the temperature range of 500 to 700° C., preferably in the temperature range of 520 to 700° C. for 1 to 20 hours. The firing can be performed using a firing furnace such as a rotary furnace, a tunnel kiln, and a muffle furnace. The average particle size of the catalyst is preferably 40 to 70 µm, and 90% or more of the catalyst particles are preferably distributed in the range of 20 to 100 µm.

[b] Step of Quenching the Butadiene-Containing Gas in a Quench Column

The production method of the present embodiment preferably comprises a step of quenching the gas containing butadiene obtained in the above [a], i.e., the gas produced in the reaction in a quench column. In this step, the gas produced in the reaction is sent to the quench column from the bottom of the column and rises within the quench column, and, since a quenching liquid is sprayed within the quench column, the gas produced in the reaction contacts the quenching liquid, is cooled and washed and evaporates from the top of the column. While cooling and washing, the components to be removed contained in the gas produced in the reaction are brought into contact with a remover contained in the quenching liquid, instead of being subjected to physical absorption such as extraction; that is, the components to be removed can be efficiently removed by a chemical adsorption in which the components are converted to those having an extremely low vapor pressure by the reaction of the components to be removed and the remover. The quench column, in the light of contacting the reaction produced gas with the quenching liquid, is preferably a multi-stage quench column having two or more compartments, more preferably having three or more compartments. In the quench column, the quenching liquid extracted in each compartment is sprayed as a circulation liquid to the upper part of the extraction site (hereinafter referred to as "circulation liquid") and becomes the extract of each compartment after cooling the reaction produced gas and removing the components to be removed. Meanwhile, the reaction produced gas containing butadiene evaporated from the top of the quench column is sent to the next step. The extracted quenching liquid is preferably sprayed again after being cooled. To reduce the load of deairing operation of the inert gas during the purification step, the outlet gas temperature of the quench column is preferably controlled to a suitable temperature. The control can be effectively achieved by cooling the quenching liquid to a suitable temperature before re-spraying and supplying the liquid to the upper stage of the quench column. At this time, the temperature of the quenching liquid is controlled to preferably 80° C. or lower, more preferably in the range from 0 to 70° C., and the outlet gas temperature of the quench column is controlled to preferably 70° C. or lower, more preferably in the range from 30 to 60° C.

The pressure of the quench column is preferably 0.01 to 0.4 MPaG, more preferably 0.02 to 0.3 MPaG, further preferably 0.03 to 0.2 MPaG.

An aqueous solution and an organic solvent can be used as the quenching liquid. When an aqueous solution is used as the quenching liquid, the pH of the liquid extracted from the upper compartments of the pipe of the quench column is preferably controlled to 7 to 12, in the lights of removal of the acidic impurities contained in the gas produced in the reaction and the safe operation. The pH of the extract can be controlled to 7 to 12 by adding to the circulation liquid of the quench column an aqueous solution containing at least one element or compound selected from the group consisting of Groups Ia and IIa. A preferred embodiment of the addition includes controlling the circulation liquid pH of the compartment stage provided at the upper part of the upper compartment in the pipe of the quench column to 7.2 to 10, preferably 7.5 to 9. Examples of the at least one element or compound selected from the Groups Ia and IIa contained in the aqueous solution to be added to control the pH of the circulation liquid is preferably at least one element or compound selected from the group consisting of sodium, potassium and magnesium, further with sodium being more preferable.

When an aqueous solution is used for the quench column, a nitrogen-containing compound, particularly an aqueous solution of an organic amine, are preferably used. When an aqueous solution of an organic amine is used, the discharged used organic amine aqueous solution can be incinerated without further treatment, hence advantageous. Examples of the organic amine used in the aqueous solution include amines such as ammonia, methylamine, ethylamine, propylamine, isopropylamine, butylamine, sec-butylamine, tert-butylamine, dimethylamine, diethylamine, dipropylamine, trimethylamine, monoethanolamine, diethanolamine, triethanolamine, N,N-dimethylethanolamine, N,N-diethylethanolamine, N,N-dibutylethanolamine, N-methylethanolamine, N-methyldiethanolamine, N-ethyl ethanolamine, N-ethyldiethanolamine, N-n-butylethanolamine, N-n-butyldiethanolamine, N-tert-butylethanolamine, N-tert-butyldiethanolamine, pyridine, aniline, pyrazole, pyrimidine, hydrazine; among these, monoethanolamine, diethanolamine, triethanolamine are preferable, with monoethanolamine being more preferable.

When an organic solvent is used as the quenching liquid, an aliphatic and/or aromatic hydrocarbon solvent can also be used. Examples of the aliphatic and/or aromatic hydrocarbon solvent includes saturated hydrocarbons having six or more carbon atoms and alkyl-substituted aromatic hydrocarbons having six or more carbon atoms. Among these, as the aliphatic hydrocarbon, heptane, octane, nonane, decane, undecane, dodecane and structural isomers thereof are preferably used. As the aromatic hydrocarbons, benzene, cyclohexane, toluene, o-xylene, m-xylene, p-xylene, mixed xylene, ethylbenzene, trimethylbenzene, cumene and pseudocumene are preferably used; toluene, o-xylene, m-xylene, p-xylene, mixed xylene, ethylbenzene are more preferably used singly or as a mixture.

In addition to the organic amine aqueous solution and the aromatic solvent, the quenching can also be carried out using water independently as a quenching liquid in each compartment of the quench column.

For the purpose of adjusting the gas-liquid contact efficiency, each compartment can be provided with spaces, trays or packed with fillers. The circulation liquid can be sprayed using a spray nozzle, and the number and the location of the nozzle can be suitably determined in consideration of the liquid and gas contact.

[c] Step of Allowing the Butadiene-Containing Gas to be Absorbed

Further, the production method of the present embodiment preferably comprises a step of allowing the butadiene-containing gas produced in the reaction to be absorbed in the solvent. The absorption of the butadiene-containing gas in a suitable solvent enables the production of a solution from which components are easily separated at the subsequent extractive distillation. Further, in the process of the absorption, the inert gases contained in the reaction produced gas are removed.

Examples of the solvent into which the butadiene-containing gas is absorbed (hereinafter also referred to as "absorption solvent") preferably include linear or cyclic saturated hydrocarbons and aromatic hydrocarbons. Specific examples of such a solvent include octane, nonane, decane, ethylcyclohexane, octene, nonene, toluene, ethylbenzene, xylene, cumene, vinylcyclohexene and furfural. Among these, octane, nonane, decane, ethylcyclohexane, toluene, m-xylene, o-xylene, p-xylene, mixed xylene, ethylbenzene and trimethylbenzene are preferably used.

In the step [c], for example, the reaction produced gas containing butadiene is cooled in the step [b] and then introduced to the bottom of the absorption column, allowed to countercurrently contact an absorption solvent in the absorption column in order to cause the butadiene and other hydrocarbons mainly having a C4 component to be absorbed from the reaction produced gas into the absorption solvent. The step [c] may also be carried out after compressing and cooling the butadiene-containing reaction produced gas.

The ratio of the absorption solvent to the C4 component contained in the reaction produced gas (absorption solvent ratio) is 1 to 30% by weight, preferably 2 to 20% by weight. The absorption solvent substantially free from hydrocarbons such as butadiene is introduced to the top of the column. The absorption column is operated at a pressure of preferably 0.1 to 1.5 MPaG, more preferably 0.2 to 1.0 MPaG at a temperature of preferably 5 to 60° C., more preferably 10 to 50° C.

Usable absorption column include columns such as packed column and plate column.

To enhance the absorption efficiency, cooling a part of the liquid in the absorption column using a cooler and suppressing the heat generation inside the absorption column is another preferred embodiment.

The butadiene-containing absorption solvent extracted from the bottom of the absorption column is preferably introduced to the step (d) in which butadiene is collected.

[d] Stripping Step

The production method of the present embodiment preferably carries out a stripping step after the above step [c]. In the stripping step, the butadiene-containing gaseous component is gasified from the butadiene-containing absorption solvent, and the absorption solvent is separated and collected. The butadiene-containing absorption solvent is preferably introduced into the middle stage of a stripping column. The stripping column is operated at a pressure of preferably 0.01 to 0.5 MPaG, more preferably 0.03 to 0.3 MPaG at a column-top temperature of preferably 0 to 90° C. and a column-bottom temperature of 100 to 190° C., more preferably 110 to 180° C. At a column-bottom temperature of 100° C. or higher, hydrocarbons such as butadiene are easily and sufficiently stripped, whereas at a temperature of 190° C. or lower, the thermal polymerization of butadiene and contaminations and tar formation can be prevented. Usable stripping column includes packed column and plate column. The butadiene-containing gas is collected from the top of the stripping column, while the absorption solvent substantially free from hydrocarbons such as butadiene is extracted from the bottom of the column. The extracted absorption solvent is continuously reusable and is hence preferably supplied to the top of the absorption column. When high boiling components, contaminations and tar removed from the reaction produced gas are accumulated in the absorption solvent due to the use over an extended period of time, the continuous or intermittent purification of the absorption solvent is another preferred embodiment. In particular, in the light of preventing the formation of the contamination and tar, a polymerization inhibitor is preferably added in advance to the absorption solvent. Examples of the polymerization inhibitor include hydroquinone, 4-methoxyphenol, phenothiazin, 2,6-di-tert-butyl-p-cresol, 2,6-di-tert-butylhydroquinone, 4-tert-butylcatechol and bisphenol A.

[e] Step of Rinsing the Liquefied Gas with Water

The production method of the present embodiment comprises a step of rinsing the liquefied gas with water. Specifically, for example, the butadiene-containing gas introduced from the above stripping step is compressed to obtain a liquefied gas, which is then brought into contact with water to extract the water-soluble components in the butadiene-containing liquefied gas, and the liquefied gas is washed. The water-soluble components, particularly acetaldehyde, are extracted and removed by allowing the liquefied gas to contact water, and the obtained liquefied gas is subjected to the [f] step of removing water to be described later. The acetaldehyde contained in the liquefied gas is preferably reduced to a trace amount by compressing the butadiene-containing gas to obtain a liquefied gas, followed by rinsing the gas with water. The removal efficiency of acetaldehyde is higher when rinsing the butadiene-containing liquefied gas with water than rinsing the gas containing gaseous butadiene with water. The reason for this is presumed by the present inventors to be that, when the area the subject to be washed contacts waterdrops (wetted surface) is the same, the liquid form has a larger amount of substance which can contact waterdrops than the gaseous form and a larger amount of acetaldehyde migrates (extracted) to the aqueous phase side, thus leading a higher water extraction efficiency. The impurity removal efficiency (water extraction efficiency) between washing the gaseous form and washing the liquefied form may also be affected by the concentration and/or the solubility to water of the substance to be extracted into the aqueous phase side in the gas or in the liquefied gas. However, at least in the purpose of removing acetaldehyde from the gas produced in the oxidative dehydrogenation reaction of a C4 or higher monoolefin, the finding that washing the liquefied gas is more efficient contributes to the accomplishment of the present invention.

The compressed and liquefied butadiene-containing gas (hereinafter simply referred to as "liquefied butadiene") is supplied from the lower part of the extraction column, water is supplied from the top of the column, the water-soluble components contained in the liquefied butadiene are extracted by the countercurrent contact of water and the liquefied butadiene in the column, followed by extracting the mixed solution of water and the liquefied butadiene from the top of the column, the mixed solution is then allowed to stand and separated to obtain the water-washed liquefied butadiene, which is subjected to the next step. The water-soluble components dissolved in the extracted water are separated by distillation or stripping, and the water from which the water-soluble components are removed is subjected again to the [e] step of rinsing with water.

The [e] step of rinsing with water is operated at a pressure of preferably 0.25 to 0.7 MPaG, more preferably 0.3 to 0.6 MPaG at an operation temperature of preferably 0 to 45° C., more preferably 5 to 30° C., further preferable 5 to 20° C.

In the [e] step of rinsing with water, columns such as packed column and plate column can be used.

In the [e] step of rinsing with water, a polymerization inhibitor is preferably added in advance to the liquefied gas phase. Examples of the polymerization inhibitor include hydroquinone, 4-methoxyphenol, phenothiazin, 2,6-di-tert-butyl-p-cresol, 2,6-di-tert-butylhydroquinone, 4-tert-butylcatechol and bisphenol A. Generally, a polymerization inhibitor is solid and exhibits the polymerization inhibitory effect while dissolved in a solvent, or the like, and thus, when a polymerization inhibitor is added to the liquefied butadiene-containing gas, the butadiene is likely to benefit the polymerization inhibitory effect in comparison with the case in which the butadiene is gaseous, hence advantageous.

[f] Step of Removing Water from the Liquefied Butadiene

The production method of the present embodiment preferably comprises a step of removing water from the liquefied butadiene. Specifically, for example, to remove water from the liquefied butadiene introduced from the above [e] step of rinsing with water, the liquefied butadiene is supplied to the upper part of the distillation column and water is extracted from the top of the column. The liquefied butadiene from which water is removed is extracted from the bottom of the column. The distillation is operated at a pressure of preferably 0.3 to 0.7 MPaG, more preferably 0.4 to 0.6 MPaG at a column top temperature of preferably 40 to 60° C. and a column bottom temperature of preferably 45 to 65° C.

In the [f] step of removing water, columns such as packed column and plate column can be used.

Water is evaporated to the top of the column by facilitating the formation of a minimum boiling azeotrope of water and butadiene at the top of the column. Butadiene and components having a higher boiling point than butadiene are concentrated at the bottom of the column. The distillation conditions under which the evaporation of the azeotropic components is facilitated are established by increasing the temperature difference between the bottom and the top of the column, whereby the butadiene-containing components with reduced moisture can be extracted from the bottom of the column.

Further, in the [f] step of removing water, a polymerization inhibitor is preferably added. Examples of the polymerization inhibitor include hydroquinone, 4-methoxyphenol, phenothiazin, 2,6-di-tert-butyl-p-cresol, 2,6-di-tert-butylhydroquinone, 4-tert-butylcatechol and bisphenol A.

[g] Step of Removing High Boiling Components from the Liquefied Butadiene

The production method of the present embodiment preferably comprises a step of removing high boiling components from the liquefied butadiene. Specifically, for example, to remove high boiling components from the liquefied butadiene extracted from the bottom of the column in the above [f] step of removing water, the liquefied butadiene is supplied to the middle stage of the distillation column and the purified liquefied butadiene is extracted from the top of the column. High boiling components such as 2-butene are extracted from the bottom of the column. The distillation is operated at a pressure of preferably 0.25 to 0.7 MPaG, more preferably 0.3 to 0.6 MPaG at a column top temperature of preferably 40 to 60° C. and a column bottom temperature of preferably 50 to 70° C.

As the separation column for high boiling components, columns such as packed column and plate column can be used.

In the [g] step of removing high boiling components, a polymerization inhibitor is preferably added. Examples of the polymerization inhibitor include hydroquinone, 4-methoxyphenol, phenothiazin, 2,6-di-tert-butyl-p-cresol, 2,6-di-tert-butylhydroquinone, 4-tert-butylcatechol and bisphenol A.

[h] Step of Removing C4 Components Other than Butadiene

The production method of the present embodiment preferably carries out a further step of removing C4 components other than butadiene from the liquefied butadiene obtained above. For example, a separate component, which significantly changes the relative volatility of each of the mixtures consisting of butadiene and C4 components other than the butadiene, is added as a solvent to the liquefied butadiene obtained in the above, and the C4 components other than the butadiene are removed from the liquefied butadiene by carrying out the extractive distillation. Specifically, the liquefied butadiene obtained above is introduced to the middle stage of the absorption column and caused to countercurrently contact the absorption solvent, whereby hydrocarbons mainly having butadiene are absorbed. Then, the extractive distillation is carried out using a solvent which significantly changes the relative volatility of butadiene and C4 components other than the butadiene, mainly butanes and butenes, to separate the butadiene. Because of the step [h], the components having three or less carbon atoms contained in a small amount in the liquefied butadiene obtained above and having a relative volatility higher than that of butadiene and derivatives thereof can be evaporated together with butanes and butenes.

A polar solvent is used as the extraction solvent used in the step [h]. The polarity used herein refers to molecular polarizability, and the indication parameter is usually expressed in the electronegativity, permittivity or dipole moment of the molecule constituent atom. The dipole moment is a physical quantity represented by the unit Debye (D), and a molecule with a high numerical value generally has the correlation with a high polarity. For example, water is represented by 1.85 D, formamide is represented by 3.4 D, acetone is represented by 2.7 D, toluene is represented by 0.4 D, o-xylene is represented by 0.7 D, m-xylene is represented by 0.4 D and p-xylene is represented by 0 D.

The extraction solvent used in the step [h] preferably includes water, alcohol, glycol, acetone, methyl ethyl ketone, methyl vinyl ketone, dioxane, dimethyl sulfoxide, propionitrile, pyridine, piperidine, pyrimidine, aniline, acetonitrile, propionitrile, N,N-dimethylformamide, N,N-dimethylacetamide, N-methylpyrrolidone, N-methyl-2-pyrrolidone, morpholine, furan, tetrahydrofuran, furfural, phenol, dimethyl carbonate, diethyl carbonate, propyl carbonate, butyl carbonate and derivatives thereof; more preferably N-alkyl-substituted lower fatty acid amide, nitrile compounds and heterocyclic compounds; further preferably N,N-dimethylformamide, N-methylpyrrolidone, N,N-dimethylacetamide and acetonitrile; a single component or a mixture of two or more selected from these is also preferable. When the extractive distillation is carried out in the step [h] using an extraction solvent having a comparatively high polarity, particularly N-alkyl-substituted lower fatty acid amide or a heterocyclic compound among nitrogen-containing compounds, the C4 components other than butadiene are much easier to remove. In addition to the polarity, the boiling point can be a criterion for solvent selection. The boiling point of the extraction solvent used in the step [h] is preferably those having a significant difference from the boiling point of the liquefied gas at a preferred pressure of the absorption column to be described later so that the solvent hardly follows into the liquefied gas and those which do not excessively raise the thermal load of the distillation column so as not to facilitate side reactions such as polymerization of butadiene.

As a result of the extractive distillation using a polar solvent in the step [h], the C4 components other than butadiene are evaporated to the top of the extractive distillation column. The absorption solvent substantially free from hydrocarbons such as butadiene is preferably introduced to the top of the absorption column. To sufficiently separate the solvent from the liquefied gas at the top of the column by providing a vapor pressure difference between the solvent and the liquefied gas, the absorption column has a pressure of preferably 0.25 MPaG or more, more preferably 0.30 MPaG or more. The upper limit of the pressure is preferably 1.5 MPaG or less, more preferably 1.0 MPaG or less, to optimize the thermal load of the distillation column and suppress side reactions such as polymerization of butadiene. The absorption column is operated, though depending on the boiling point, etc. of the solvent, at a temperature of preferably 50 to 200° C., more preferably 80 to 180° C., in the lights of the separation and the thermal load.

Another preferred embodiment is to comprise this step [h] before the "[e] step of rinsing with water." Due to such a step order, the extraction solvent for the nitrogen-containing compound entrained in the butadiene in the extractive distillation step [h] and the pyrolysate thereof (e.g., dimethylamine and formic acid) can be extracted or distilled and separated in the following [e] step of rinsing with water.

Among the byproduced oxides, carbonyl compounds, e.g., acetaldehyde, form a minimum boiling azeotrope which causes azeotropy at a temperature lower than the boiling point of butadiene and both components. The azeotropic point of this azeotrope is −5° C., which is extremely close to the boiling point of butadiene −4° C. Consequently, acetaldehyde is one of the interfering components against the high purity purification of butadiene. The separation of a minimum boiling azeotrope whose boiling point is extremely close to the boiling point of the component to be purified requires an enormous distillation stages when the typical distillation operation is employed, practically failing to apply in an industrial scale.

Conversely, performing the [h] step of washing the liquefied gas with a polar solvent before the [e] step of rinsing with water enables the even further reduction of the acetaldehyde concentration. Due to such a step order, a state in which acetaldehyde almost does not coexist is achieved, which is hence preferable to extract butadiene from the top of the distillation column and collect high purity butadiene without being affected by the above-mentioned azeotropy. It is also conceivable to extract butadiene from the middle stage of the column, so-called side cut, instead of the top of the column. However, the thorough separation of acetaldehyde from butadiene is also hardly achieved in this case, and thus, in the light of the further reduction of acetaldehyde, the extraction from the top of the column is a preferred embodiment.

When the "[h] step of removing a C4 fraction other than butadiene" is carried out after the "[g] step of removing high boiling components from the liquefied butadiene", the existing butadiene extractive distillation apparatus, i.e., the DMF extractive distillation apparatus for C4 components derived from naphtha cracking, can be simply used, hence advantageous.

[i] Stripping Step

The production method of the present embodiment preferably carries out, after the above step [h], the gasification of a butadiene-containing gaseous component from a butadiene-containing absorption solvent and the separation and collection of the absorption solvent. The butadiene-containing absorption solvent is preferably introduced to the middle stage of the stripping column. The stripping column is operated at a pressure of preferably 0.03 to 0.5 MPaG, more preferably 0.05 to 0.3 MPaG at a column top temperature of preferably 0 to 90° C. and a column bottom temperature of preferably 100 to 190° C., more preferably 110 to 180° C. At a column-bottom temperature of 100° C. or higher, hydrocarbons such as butadiene are likely to be sufficiently stripped, whereas a temperature of 190° C. or lower can prevent the formation of polymers and tar. When the high boiling components, contaminations and tar removed from the reaction produced gas are accumulated in the absorption solvent due to the use over an extended period of time, the continuous or intermittent purification of the absorption solvent is another preferred embodiment. In particular, in the light of preventing the formation of contaminations and tar, a polymerization inhibitor is preferably added in advance to the absorption solvent. Examples of the polymerization inhibitor include hydroquinone, 4-methoxyphenol, phenothiazin, 2,6-di-tert-butyl-p-cresol, 2,6-di-tert-butylhydroquinone, 4-tert-butylcatechol and bisphenol A.

Usable stripping columns include packed column and plate column. The butadiene-containing gas is collected from the top of the stripping column, while the absorption solvent substantially free from hydrocarbons such as butadiene is extracted from the bottom of the column. The bottom liquid, after being adjusted to a predetermined temperature through a heat exchanger is reusable as the absorption solvent, and thus preferably introduced to the top of the absorption column. Since the absorption solvent becomes contaminated with the high boiling substances, tar, etc., when used over an extended period of time, the continuous or intermittent purification of the solvent is preferred. In the light of preventing contaminations, a polymerization inhibitor is preferably added to the absorption solvent.

The steps [h] and [i] are preferably carried out between the step [d] and the step [e] or after the step [g]. The steps [h] and [i] may be left out when the butadiene-containing C4 components to be subjected to the steps [h] and [i] contains a small amount of C4 component such as butane and butene.

EXAMPLES

Hereinafter, the present invention will be described further in detail with reference to Examples; however, the present invention is not limited to Examples to be described below.

(Reaction Results)

The n-butene conversion, the butadiene selectivity, and the yield that have been used for indicating the reaction results were defined by the following formulas:

$$\text{n-butene conversion (\%)} = \frac{\text{(the number of moles of n-butene reacted)}}{\text{(the number of moles of n-butene supplied)}} \times 100 \quad \text{[Expression 2]}$$

$$\text{Butadiene selectivity (\%)} = \frac{\text{(the number of moles of butadiene produced)}}{\text{(the number of moles of n-butene reacted)}} \times 100 \quad \text{[Expression 3]}$$

$$\text{Butadiene yield (\%)} = \frac{\text{(the number of moles of butadiene produced)}}{\text{(the number of moles of n-butene supplied)}} \times 100 \quad \text{[Expression 4]}$$

(Contact Time)

The contact time was defined by the following formula:

$$\text{Contact time (g·sec/cc)} = \frac{W \times 60 \times 273.15 \times (P \times 1000 + 101.325)}{F \times (273.15 + T) \times 101.325} \quad \text{[Expression 5]}$$

In the formula, W represents the filling amount of a catalyst (g); F represents the flow rate of a raw material mixed gas (cc/min, in terms of NTP (0° C., 1 atm)); T represents the reaction temperature (° C.); and P represents the reaction pressure (MPa).

(Analysis of Oxygen)

The analysis of oxygen at the reactor exit was conducted using gas chromatography (GC-8A (manufactured by Shimadzu), analysis column: ZY1 (manufactured by Shinwa Chemical Industries, Ltd.), carrier gas: helium, column temperature: constant at 75° C., TCD preset temperature: 80° C.) connected directly to the reactor.

(Analysis of Unreacted Compound and Reaction Products)

The analysis of unreacted n-butene and reaction products such as butadiene and methacrolein was conducted using gas chromatography (GC-2010 (manufactured by Shimadzu), analysis column: HP-ALS (manufactured by J&W), carrier gas: helium, column temperature: maintained at 100° C. for 8 minutes after gas injection, then increased to 195° C. at a rate of 10° C./minute, and then maintained at 195° C. for 40 minutes, TCD-FID (hydrogen flame ion detector) preset temperature: 250° C.) connected directly to the reactor.

Example 1

(a) Catalyst Preparation

An oxide represented by a composition of $Mo_{12}Bi_{0.60}Fe_{1.8}Ni_{5.0}K_{0.09}Rb_{0.05}Mg_{2.0}Ce_{0.75}$ was supported on 50% by weight silica to prepare a catalyst as follows. To 1835.4 g of silica sol containing 30% by weight $SiO_2$, was added a solution of 58.7 g of bismuth nitrate [Bi$(NO_3)_3.5H_2O$], 65.7 g of cerium nitrate [Ce$(NO_3)_3.6H_2O$], 146.7 g of iron nitrate [Fe$(NO_3)_3.9H_2O$], 293.4 g of nickel nitrate [Ni$(NO_3)_2.6H_2O$], 103.5 g of magnesium nitrate [Mg$(NO_3)_2.6H_2O$], 1.8 g of potassium nitrate [$KNO_3$], and 1.5 g of rubidium nitrate [$RbNO_3$] in 413.3 g of 16.6% by weight nitric acid, and thereto was finally added a solution of 427.4 g of ammonium paramolybdate [$(NH_4)_6Mo_7O_{24}.4H_2O$] in 860.9 g of water. The raw material mixed liquid obtained here was sent to a parallel flow spray dryer, wherein it was dried at an inlet temperature of about 250° C. and an outlet temperature of about 140° C. The mixed liquid was atomized using an atomization apparatus provided with a dish rotator installed in the upper center of the dryer. The resulting powder was pre-fired at 350° C. for one hour in an air atmosphere in an electric furnace and then fired at 590° C. for two hours in an air atmosphere to obtain a catalyst.

(b) Butadiene Production Reaction 1300 g of the catalyst obtained in the above (a) Catalyst preparation step was charged into a reactor made of SUS304 having a tube diameter of 3 inches and a height of 950 mm. To this reaction tube were supplied raw materials of, as components having four carbon atoms (hereinafter also referred to as "C4 raw material"), n-butene:n-butane:isobutane:isobutene=53.9:37.0:8.4:0.7 (weight ratio) at 405.9 g/Hr, oxygen and nitrogen at 106.56 g/Hr and 816.3 g/Hr, respectively, and the reaction was carried out under the conditions of a reaction temperature T=360° C. and a reaction pressure P=0.05 MPa, thereby obtaining the reaction produced gas. At this time, the contact time between the catalyst and the mixed gas (C4 raw materials, oxygen and nitrogen) was 2.9 (g·sec/cc).

After the lapse of 24 hours from the start of the reaction, the obtained gas produced in the reaction was analyzed and the reaction performance was found to have 95.5% of n-butene conversion; 83.1% of butadiene selectivity; and 79.4% of butadiene yield.

(c) Quench of Reaction Gas

The reaction produced gas obtained in the above step (b) was introduced to the lower stage of a quench column (made of SUS304 having a quench compartment (tube diameter 100 mm, height 1000 mm) at the upper part of the column bottom (tube diameter 200 mm, height 300 mm)), thereby obtaining a discharge gas from the top of the quench column. The quench compartment in the quench column was three-staged. The liquid extracted from the bottom of the column was sprayed at 90, 180 and 180 L/Hr to the upper stage, middle stage and lower stage of the three-staged quench compartment, respectively. To the spray liquid for the middle stage was added an aqueous solution of 10% by weight sodium hydroxide so that the bottom extract had a pH of 7.6. Further, the spray liquid for the upper stage was cooled to 47° C. through a heater exchanger before spraying. At this time, the discharge gas temperature from the top of the quench column was 53° C.

(d) Step of Absorbing C4 Component

The discharged gas obtained in the above step (c) was compressed to 0.5 MPaG using a compressor and introduced to the lower stage of an absorption column (made of SUS304 having a pipe diameter of 2.5 inches, a height of 3300 mm, packed with Raschig ring having a 5 mm φ*5 mm inside the column) while being controlled at 50° C. through a heat exchanger. m-Xylene (boiling point: 139.1° C.), cooled to 10° C., was supplied to the upper stage of the absorption column at 5.0 kg/Hr and allowed to countercurrently contact the above discharge gas introduced from the lower stage, whereby the C4 components containing 99.8% of the butadiene in the discharge gas were absorbed into m-xylene. The 50° C. m-xylene which absorbed the C4 components was extracted from the bottom of the column.

(e-1) Step of Collecting C4 Component m-Xylene absorbed the C4 components obtained in the above step (d) was introduced into the middle stage of a collection column (made of SUS304 having a pipe diameter of 2.5 inches, a height of 3000 mm, packed with Raschig ring having a 5 mmφ*5 mm inside the column). The collection column was operated so as to have a pressure of 0.11 MPaG, a column bottom temperature of 110° C. and a column top gas temperature of 25° C. A gas containing 50.2% by weight of butadiene was obtained from the top of the collection column. The obtained butadiene-containing gas was compressed to 0.6 MPaG to obtain a liquefied gas, which was extracted at 332 g/Hr. Butadiene free x-xylene was extracted at 5.0 kg/Hr from the bottom of the collection column and supplied as the absorption liquid of the above step (d).

(f) Step of Rinsing

The butadiene-containing liquefied gas obtained in the above step (e-1) was supplied at a rate of 332 g/Hr to the bottom of a rinse column (made of SUS304 having a pipe diameter of 3 inches, a height of 2500 mm, and packed with Raschig ring inside the column). The rinse column was operated so as to have a pressure of 0.6 MPaG and column bottom and column top temperatures of 25° C. In this step, the liquefied gas contained 6500 ppm by weight of acetaldehyde before being supplied to the rinse column. Water was supplied at a rate of 4.0 kg/Hr from the top of the rinse column and allowed to countercurrently contact the liquefied gas supplied from the bottom of the column, thereby rinsing the liquefied gas with water. Oil-water separation of the liquid extracted from the top of the rinse column was carried out, thereby obtaining the liquefied gas at a rate of 329 g/Hr. The acetaldehyde content in this butadiene-containing liquefied gas was 12 ppm by weight.

Comparative Example 1

The operation was carried out in the same manner as in Example 1 except that the obtained butadiene-containing gas was not compressed in the step (e-1) described in Example 1 and the gas containing the non-compressed butadiene was supplied to the bottom of the rinse column (made of SUS304 having a pipe diameter of 600 mm, a height of 2500 mm), and water was supplied by spraying at a rate of 4 kg/Hr from the top of the rinse column in the step (f) described in Example 1. The acetaldehyde content in the gas extracted from the top of the rinse column was 2800 ppm by weight.

Example 2

After the steps (a) to (f) described in Example 1, the following steps (g) and (h) were further carried out.
(g) Step of Removing Water The butadiene-containing liquefied gas extracted from the column top in the step (f) described in Example 1 was temporarily stored in a tank, and introduced to the upper stage of a dehydration column (made of SUS304 having 36 staged trays and a pipe diameter of 2.5 inches and a height of 3000 mm) at 329 g/Hr. The dehydration column was operated so as to have a pressure of 0.60 MPaG, a column bottom temperature of 53° C. and a column top gas temperature of 51° C. In the dehydration column, water and the butadiene-containing liquefied gas were allowed to pass through an oil separator from the top of the column and extracted to outside the system at 0.2 g/Hr, whereas the liquefied gas substantially does not contain water but contains butadiene was extracted from the bottom of the column at 329 g/Hr.
(h) Step of Removing High Boiling Component The butadiene-containing liquefied gas extracted from the bottom of the column in the above step (g) was introduced to the middle stage of a distillation column (made of SUS304 having 52 staged trays and having a pipe diameter of 2.5 inches and a height of 3300 mm). The distillation column was operated so as to have a pressure of 0.60 MPaG, a column bottom liquid temperature of 61° C. and a column top gas temperature of 52° C. The liquefied gas containing C4 components such as butadiene was extracted from the top of the distillation column at a rate of 326 g/Hr. In this liquefied gas, the purity of butadiene was 51.1% by weight, the acetaldehyde content in the butadiene-containing liquefied gas was 12 ppm by weight and the low boiling components having three or less carbon atoms was 30 ppm by weight. Also, the butadiene-containing liquefied gas containing 41% by weight of the high boiling components was extracted from the bottom of the column at 6 g/Hr.

Comparative Example 2

The following step equivalent to the step of removing water was operated after the steps (a) to (c) among the steps described in Example 1.

The discharge gas obtained in the step (c) described in Example 1 was compressed to 0.5 MPaG and supplied to the dehydration column (a pipe diameter 3 inches) packed with 1.5 kg of molecular sieve 3A while controlling the temperature at 50° C. through a heat exchanger, thereby removing water from the discharge gas.

Subsequently, the operation for collecting the butadiene-containing C4 components was carried out in the order of the (d) step of absorbing C4 components described in Example 1, the (e-1) step of collecting C4 components described in Example 1 and the (h) step of removing high boiling component described in Example 2. The operation was continued for 9 hours or longer with no serious problems. However, after the lapse of 10 hours from the start of the operation, the water content in the collected butadiene-containing C4 components started to rise at the completion of the step (h) and increased to 770 ppm by weight, and after the lapse of 23 hours from the start of the operation, the high boiling components are deposited on and blocked the fillers, failing to control the pressure and making it difficult to operate safely, whereby the operation came to a halt.

Example 3

The liquefied gas was obtained from the top of the rinse column under the same conditions as in Example 1 except that the water amount to be supplied to the top of the rinse column was changed to 8.0 kg/Hr in the step (f) described in Example 1. Further, the operation was carried out to the (g) step of removing water and the (h) step of removing high boiling component described in Example 2, whereby butadiene was collected. At this time, in the step (h), a liquid containing 50.8% by weight of butadiene and 3 ppm by weight of acetaldehyde was collected at 324 g/Hr from the top of the distillation column.

Example 4

The liquefied gas was obtained from the top of the rinse column under the same conditions as in Example 1 except that the water amount to be supplied to the top of the rinse column was changed to 2.5 kg/Hr in the step (f) described in Example 1. Further, the operation was carried out to the (g) step of removing water and the (h) step of removing high boiling component described in Example 2, whereby butadiene was collected. At this time, in the step (h), a liquid containing 51.1% by weight of butadiene and 31 ppm by weight of acetaldehyde was collected at 326 g/Hr from the top of the distillation column.

Example 5

The operation was carried out in the steps (a) to (e-1) described in Example 1, thereby obtaining the butadiene-containing liquefied gas.
(e-2) Step of Absorbing Butadiene Component The butadiene-containing liquefied gas obtained in the step (e-1) described in Example 1 was introduced into the lower stage of an absorption column (made of SUS304 having a pipe diameter of 2.5 inches, a height of 3200 mm, packed with Raschig ring having a 6 mmϕ*6 mm inside the column). The column top pressure of the absorption column was 0.45 MPaG. To the upper stage of the absorption column was supplied N,N-dimethylformamide (hereinafter also referred to as "DMF", boiling point: 153° C.), cooled to 15° C., at 4.5 kg/Hr, allowed to countercurrently contact the liquefied gas introduced from the lower stage, whereby extractive distillation was carried out. In the absorption column, the gas containing butane (n-butane and isobutane) and low boiling compounds was extracted at 161 g/hr from the top of the column while controlling the column bottom temperature at 140° C., thereby extracting from the bottom of the column DMF in which the butadiene-containing C4 components are dissolved.
(e-3) Step of Collecting Butadiene Component The butadiene-containing DMF obtained in the above step (e-2) was introduced to the middle stage of the collection column (made of SUS304 having a pipe diameter of 2.5 inches, a height of 3500 mm, packed with Raschig ring having a 6 mmϕ*6 mm inside the column). The collection column was operated so as to have a pressure of 0.15 MPaG, a column bottom temperature of 140° C. and a column top gas temperature of 30° C. The liquefied gas containing 96.5% by weight of butadiene was extracted at 166 g/Hr from the column top, while the butadiene free DMF was extracted at 4.5 kg/Hr from the column bottom, and supplied as the absorption liquid of the above step (e-2).

Using the butadiene-containing liquefied gas obtained from the column top, the operation was carried out in the same manner as operated in the (f) step of rinsing described in Example 1, the (g) step of removing water and the (h) step of removing high boiling component described in Example 2, thereby extracting at 169 g/Hr from the top of the distillation column a liquid containing 98.0% by weight of butadiene and 9 ppm by weight of acetaldehyde. In the extracted butadiene-containing liquid, low boiling components having three or less carbon atoms were not found.

Example 6

An operation was carried out to the (h) step of removing high boiling component in the same manner as in Example 5 except that monoethanolamine was used in place of an aqueous solution of 10% by weight of sodium hydroxide in the step (c) and the rate of water supply in the step (f) was changed to 2.0 kg/Hr, thereby collecting butadiene. At this time, in the step (h), a liquid containing 98.0% by weight of butadiene and 5 ppm by weight of acetaldehyde was collected at 168 g/Hr from the top of the distillation column. In the extracted butadiene-containing liquid, low boiling components having three or less carbon atoms were not found.

Example 7

An operation was carried out to the (h) step of removing high boiling component in the same manner as in Example 5 except that the column bottom temperature was changed to 155° C. in the step (e-2), thereby collecting butadiene. At this time, in the step (h), a liquid containing 99.4% by weight of butadiene and 8 ppm by weight of acetaldehyde was collected at 167 g/Hr from the top of the distillation column. In the collected butadiene-containing liquid, low boiling components having three or less carbon atoms were not found.

Example 8

An operation was carried out to the (h) step of removing high boiling component in the same manner as in Example 5 except that the column bottom temperature was changed to 120° C. in the step (e-2), thereby collecting butadiene. At this time, in the step (h), a liquid containing 97.8% by weight of butadiene and 9 ppm by weight of acetaldehyde was collected at 169 g/Hr from the top of the distillation column. The collected butadiene-containing liquid contained 5 ppm by weight of the low boiling components having three or less carbon atoms.

Example 9

An operation was carried out to the (h) step of removing high boiling component under the same conditions as in Example 5 except that the DMF supply amount was changed to 2.5 kg/Hr in the step (e-2) and the extraction amount of the butadiene free DMF from the column bottom was changed to 2.5 kg/Hr in the step (e-3), thereby collecting butadiene. At this time, in the step (h), a liquid containing 98.2% by weight of butadiene and 9 ppm by weight of acetaldehyde was collected at 169 g/Hr from the top of the distillation column. The collected butadiene-containing liquid contained 10 ppm by weight of the low boiling components having three or less carbon atoms.

Example 10

An operation was carried out to the (h) step of removing high boiling component under the same conditions as in Example 5 except that the DMF supply amount was changed to 6 kg/Hr in the step (e-2) and the extraction amount of the butadiene free DMF from the column bottom was changed to 6 kg/Hr in the step (e-3), thereby collecting butadiene. At this time, in the step (h), a liquid containing 98.7% by weight of butadiene and 9 ppm by weight of acetaldehyde was collected at 168 g/Hr from the top of the distillation column. In the collected butadiene-containing liquid, low boiling components having three or less carbon atoms were not found.

Example 11

An operation was carried out to the (h) step of removing high boiling component under the same conditions as in Example 5 except that DMF to be supplied was changed to N,N-dimethylacetamide in the step (e-2), thereby collecting butadiene. At this time, in the step (h), a liquid containing 98.0% by weight of butadiene and 6 ppm by weight of acetaldehyde was collected at 169 g/Hr from the top of the distillation column. In the collected butadiene-containing liquid, low boiling components having three or less carbon atoms were not found.

Example 12

An operation was carried out to the (h) step of removing high boiling component under the same conditions as in Example 5 except that DMF to be supplied was changed to N-methylpyrrolidone in the step (e-2), thereby collecting butadiene. At this time, in the step (h), a liquid containing 97.7% by weight of butadiene and 8 ppm by weight of acetaldehyde was collected at 170 g/Hr from the top of the distillation column. In the collected butadiene-containing liquid, low boiling components having three or less carbon atoms were not found.

Example 13

An operation was carried out to the (h) step of removing high boiling component under the same conditions as in Example 5 except that DMF to be supplied was changed to acetonitrile in the step (e-2), thereby collecting butadiene. At this time, in the step (h), a liquid containing 95.4% by weight of butadiene and 10 ppm by weight of acetaldehyde was collected at 169 g/Hr from the top of the distillation column. The collected butadiene-containing liquid contained 5 ppm by weight of the low boiling components having three or less carbon atoms.

Example 14

An operation was carried out to the (h) step of removing high boiling component under the same conditions as in Example 5 except that DMF to be supplied was changed to ethanol in the step (e-2), thereby collecting butadiene. At this time, in the step (h), a liquid containing 91.2% by weight of butadiene and 14 ppm by weight of acetaldehyde was collected at 165 g/Hr from the top of the distillation column. The collected butadiene-containing liquid contained 12 ppm by weight of the C3 or lower low boiling components.

Example 15

An operation was carried out for twelve hours under the same conditions as in Example 5 except that the butadiene-containing liquefied gas obtained in the step (g) in Example 2 was subjected to the step (e-2) in Example 5, thereby collecting butadiene. At this time, in the step (h), a liquid containing 98.1% by weight of butadiene and 8 ppm by weight of acetaldehyde was extracted at 166 g/Hr from the top of the distillation column. The extracted butadiene-containing liquid contained 11 ppm by weight of the low boiling components having three or less carbon atoms and 3 ppm by weight of dimethylamine.

INDUSTRIAL APPLICABILITY

According to the production method of the present invention, when a conjugated diolefin is produced by the oxidative dehydrogenation reaction of an n-butene-containing C4 component represented by BBSS and a molecular oxygen-containing gas using a metal oxide catalyst, a high purity conjugated diolefin usable as a raw material for synthetic rubbers and resins can be produced even when the reaction produced gas contains, for example, side reaction products represented by C4 components and inert gas components which do not contribute to the reaction, unreacted n-butenes, an oxygen-containing compound such as acetaldehyde.

What is claimed is:
1. A method for production of a conjugated diolefin, wherein said method comprises the following steps of (1) to (6) in this order:
    step (1): a step of supplying a source gas containing a C4 or higher monoolefin and an oxygen-containing gas into a reactor to form a gas mixture and bringing a catalyst into contact with the gas mixture to obtain a gas containing a conjugated diolefin by an oxidative dehydrogenation reaction,
    step (2): a step of cooling the gas containing the conjugated diolefin in a quench column,
    step (3): a step of allowing the gas containing the conjugated diolefin to be absorbed in a solvent, subsequently stripping the gas containing the conjugated diolefin from the solvent, followed by compressing the gas to obtain a liquefied gas, wherein the solvent for absorbing the gas containing the conjugated diolefin is toluene, m-xylene, o-xylene, p-xylene, or mixed xylene,
    step (4): a step of rinsing the liquefied gas with water,
    step (5): a step of removing the water from the liquefied gas by distillation, and
    step (6): a step of removing a high boiling component from the liquefied gas, wherein
    in the step (1), an oxygen concentration of the gas containing the conjugated diolefin is in a range of 0.01 to 2.0% by volume.
2. The method for production of the conjugated diolefin according to claim 1,
    wherein the liquefied gas obtained in the step (3) contains acetaldehyde, and
    the acetaldehyde is dissolved in the water in the step (4).
3. The method for production of the conjugated diolefin according to claim 1, further comprising, before the step (4) and/or after the step (6), a step of:
    allowing the liquefied gas to be absorbed in a high polarity solvent having a higher polarity than the solvent of the step (3), subsequently stripping the gas containing the conjugated diolefin from the high polarity solvent, followed by compressing the gas to obtain a liquefied gas.
4. The method for production of the conjugated diolefin according to claim 3, wherein the high polarity solvent contains at least one selected from the group consisting of N-alkyl-substituted lower fatty acid amide, a nitrile compound and a heterocyclic compound.
5. The method for production of the conjugated diolefin according to any one of claims 1 and 2-4, wherein the source gas contains n-butene.
6. The method for production of the conjugated diolefin according to claim 1,
    wherein the source gas and the oxygen-containing gas are independently supplied into the reactor in the step (1).
7. The method for production of the conjugated diolefin according to claim 1,
    wherein the catalyst is represented by a following formula:

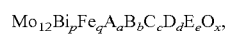

where A is at least one element selected from the group consisting of nickel and cobalt; B is at least one element selected from the group consisting of alkali metal elements; C is at least one element selected from the group consisting of magnesium, calcium, strontium, barium, zinc, and manganese; D is at least one rare earth element; E is at least one element selected from the group consisting of chromium, indium, and gallium; O is oxygen; p, q, a, b, c, d, e, and x represent an atomic ratio of bismuth, iron, A, B, C, D, E, and oxygen, respectively, to 12 molybdenum atoms; $0.1 \leq p \leq 5$, $0.5 \leq q \leq 8$, $0.1 \leq a \leq 10$, $0.02 \leq b \leq 2$, $0 \leq c \leq 5$, $0 \leq d \leq 5$, and $0 \leq e \leq 5$ are satisfied; and x is an atomic number of oxygen required for satisfying a valence requirement of the other elements.
8. The method for production of the conjugated diolefin according to claim 1, wherein the step (4) of rinsing the liquefied gas with water is performed at an operation temperature of 5 to 45° C.
9. The method for production of the conjugated diolefin according to claim 1, wherein the solvent for absorbing the gas containing the conjugated diolefin is m-xylene, o-xylene, p-xylene, or mixed xylene.
10. The method for production of the conjugated diolefin according to claim 1, wherein the step (4) of rinsing the liquefied gas with water is operated at a pressure of 0.25 to 0.7 MPaG.
11. The method for production of the conjugated diolefin according to claim 1, wherein the step (5) of removing the water from the liquefied gas by distillation is operated at a pressure of 0.3 to 0.7 MPaG.
12. The method for production of the conjugated diolefin according to claim 1, wherein the step (5) of removing the water from the liquefied gas by distillation is operated at a column top temperature of 40 to 60° C. and a column bottom temperature of 45 to 65° C.
13. The method for production of the conjugated diolefin according to claim 1, wherein the step (5) of removing the water from the liquefied gas by distillation is performed in a packed column or a plate column.
14. The method for production of the conjugated diolefin according to claim 1, wherein the step (5) of removing the water from the liquefied gas by distillation further comprises adding a polymerization inhibitor.

15. The method for production of the conjugated diolefin according to claim 14, wherein the polymerization inhibitor comprises at least one of hydroquinone, 4-methoxyphenol, phenothiazine, 2,6-di-tert-butyl-p-cresol, 2,6-di-tert-butyl-hydroquinone, 4-tert-butylcatechol, and bisphenol A.

16. The method for production of the conjugated diolefin according to claim 1, wherein the step (6) of removing the high boiling component from the liquefied gas is operated at a pressure of 0.25 to 0.7 MPaG.

17. The method for production of the conjugated diolefin according to claim 1, wherein the step (6) of removing the high boiling component from the liquefied gas is operated at a column top temperature of 40 to 60° C. and a column bottom temperature of 50 to 70° C.

18. The method for production of the conjugated diolefin according to claim 1, wherein the step (6) of removing the high boiling component from the liquefied gas is performed in a packed column or a plate column.

19. The method for production of the conjugated diolefin according to claim 1, wherein the step (6) of removing the high boiling component from the liquefied gas further comprises adding a polymerization inhibitor.

20. The method for production of the conjugated diolefin according to claim 19, wherein the polymerization inhibitor comprises at least one of hydroquinone, 4-methoxyphenol, phenothiazine, 2,6-di-tert-butyl-p-cresol, 2,6-di-tert-butyl-hydroquinone, 4-tert-butylcatechol, and bisphenol A.

\* \* \* \* \*